Oct. 8, 1963 J. L. HEVENER Plant Pat. 2,288
APPLE TREE
Filed Oct. 24, 1960
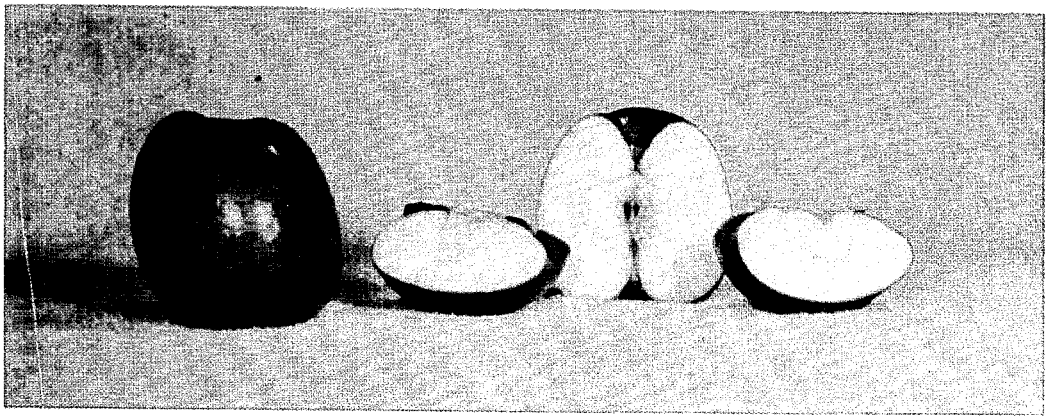
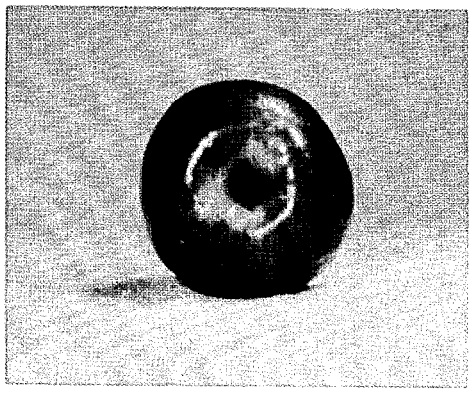
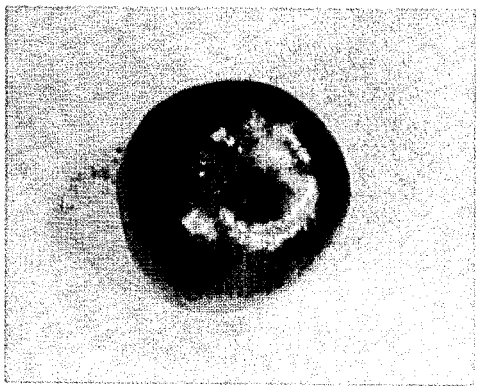

United States Patent Office

Plant Pat. 2,288
Patented Oct. 8, 1963

2,288
APPLE TREE

John L. Hevener, Roanoke, W. Va.

Filed Oct. 24, 1960, Ser. No. 64,687
1 Claim. (Cl. Plt.—34)

The present invention relates to a new and distinct variety of apple tree which was discovered by me as a bud sport of the variety known commercially and popularly as the "York Imperial."

The fruit borne by this tree is a deep, dull red in color, has the characteristic shape of the common York Imperial, the average size or diameter of the apple is approximately three inches, the keeping quality of the said apple is very good and may be kept for as much as ten months without special attention of any kind, the tree on which said apple grows is a partial dwarf, the calyx end of the apple is much deeper than the common York Imperial, the core of the apple is less than half the length of the apple, the tree has been grafted and observed for fifteen years and has borne continuously for nine years, the apple ripens approximately one to two weeks later than the common York Imperial, the apple will color a deep dull red even in the shade, the apple has a skin that is approximately twice as thick as the common York Imperial. Fruit spurs develop approximately two years earlier than the common York Imperial, and as compared to the latter the new variety has a fuller development of red color as particularized below.

Asexual reproduction of the new variety by budding, as performed by me in the orchard of the Roanoke Nursery at Roanoke, West Virginia, shows that the foregoing characteristics and distinctions come true to form and are established and transmitted through succeeding propogations.

The new variety differs over the "Yorking" apple, which is the nearest known variety, principally in that the new variety has a deeper calyx end, thicker skin and smaller core.

The following is a detailed description of my new variety, with color terminology being in accordance with the Dictionary of Color by Maerz and Paul, Second Edition, published 1950, except where color terms of ordinary significance are obvious:

Date of first pickings: about October 15th.

Tree: Medium, vigorous, low, hardy, very productive, regular bearer.

Trunk: Smooth and stocky.

Branches: Smooth, thick, spready, color—grey-green.

Leaves: Medium large; medium width; ovate; abruptly pointed; thick.

Flowers: Full bloom approximately May 1.

*Size.*—Medium large to large.

*Color.*—White, with portions of petals tinged with pink.

Fruit: Maturity—October 15.

*Size.*—Uniform; axial diameter 3 inches; transverse diameter 3 inches.

Form: Conical, slightly angular.

Cavity: Symmetrical.

Basin: Symmetrical; flaring base, depth ½ inch; breadth, ½ inch; color, yellowish olive.

Stem: Clubbed, medium stout, length, ⅛ inch; breadth, ⅛ inch.

Calyx: Very deep, ¾ inch.

Skin: Thick, tough, smooth, waxed. Dots, many small; circular; color cartridge, buff; distribution over entire surface. Color, slightly lighter than Plate 5, L–9, Dictionary of Color, by Maerz and Paul.

Flesh: Rather juicy; color, satiny white.

*Texture.*—Firm, fine, crisp.

*Flavor.*—Mild, rich.

*Aroma.*—Distinct.

*Quality.*—Best.

Core: Bundle area extremely small; halves of core equal.

Seeds: Average number (six to eight); form, acute; color, chestnut brown.

Use: Market; dessert.

Keeping quality: Good, about 120 days in ordinary storage.

I claim:

A new and distinct variety of apple tree, substantially as herein shown and described, characterized particularly as to novelty by improved shape and deeper red coloring, earlier development of fruit spurs, later ripening, thicker skin and excellent longer keeping quality in storage as compared to the fruit of the variety "York Imperial" of which the new variety is a bud sport.

No references cited.